United States Patent [19]

Szánya et al.

[11] Patent Number: 5,382,655

[45] Date of Patent: Jan. 17, 1995

[54] PROCESS FOR THE PURIFICATION OF CYCLOSPORIN A

[75] Inventors: Tibor Szánya, Veszprém; Lászlo Hanák, Boldogköujfalu; Gyöngyi Strbka, Veszprém; Edit Nagy, Debrecen; István Melczer, Debrecen; György Deák, Debrecen; Berta Makó, Debrecen; Anita Karczub, Hajdunánás; János Bálint, Debrecen; Ferenc Radnai, Debrecen; Ernö Karácxony, Debrecen; Csaba Hajdufi, Debrecen; Vilmos Kéri, Debrecen; Gyula Márton, Veszprém; Judit Dencs, Veszprém; János Kelemen, Veszprém, all of Hungary

[73] Assignee: Biogal Gyógyszerárugyár RT, Debrecen, Hungary

[21] Appl. No.: 66,857

[22] Filed: May 25, 1993

[30] Foreign Application Priority Data

May 25, 1992 [HU] Hungary ............................ P9201728

[51] Int. Cl.6 ........................ A61K 37/02; C07K 7/50; C07C 103/52
[52] U.S. Cl. ..................................... 530/317; 530/323
[58] Field of Search ......................................... 530/317

[56] References Cited

U.S. PATENT DOCUMENTS

| 4,117,118 | 9/1978 | Härri et al. | 530/317 |
| 4,215,199 | 7/1980 | Härri et al. | 530/317 |
| 4,554,351 | 11/1985 | Wenger | 930/20 |
| 5,116,816 | 5/1992 | Dreyfuss et al. | 530/317 |

Primary Examiner—Lester L. Lee
Assistant Examiner—P. Lynn Touzeau
Attorney, Agent, or Firm—Schweitzer, Cornman & Gross

[57] ABSTRACT

A process is disclosed for the solution chromatographic purification of cyclosporin A from a starting mixture containing one or more of cyclosporin A, B, C, other cyclosporin components that are more polar or more apolar than cyclosporin A, and other like contaminants, by heating the starting mixture or an evaporation residue thereof to a temperature from about 80° C. to about 115° C., melting the heated starting mixture, and carrying out solution chromatography of the melted material, suitably first in a 48:50:2 mixture of chloroform, dichloromethane, and ethanol, and then in a mixture of like proportions, of the solvents chloroform, ethylacetate, and ethanol.

10 Claims, 2 Drawing Sheets

PROCESS FOR THE PURIFICATION OF CYCLOSPORIN A

FIELD OF THE INVENTION

The present invention relates to a process for the purification of cyclosporin A from mixtures containing especially cyclosporins A, B, C and other cyclosporin components more polar or more aploar than cyclosporin A or contaminations similar to them.

BACKGROUND OF THE INVENTION

Cyclosporin antibiotics are prepared by fermentation. For the first time Swiss patent No. 589,716 reported the isolation of cyclosporins A and B obtained by cultivating the fungus strain *Cylindrocarpon lucidum Booth* 5760. 25 cyclosporins have been known so far, which are designated by letters A and Z, as reported in Helv. Chim. Acta 70, 13 (1987).

The different components, the chemical and physical properties of which, which are very close to each other, are isolated from the fermentation liquor by extraction. The components are separated from the thus obtained crude cyclosporin mixture by a multistep chromatographic preparative method. Although cyclosporin A which has a selective immunosuppressive activity is the most valuable among the components of the cyclosporin complex, the other components are generally also isolated and purified.

According to a method described in U.S. Pat. No. 4,117,118 the cyclosporin mixture is transferred first to a Sephadex LH20 column and eluted with methanol, then it is eluted successively in an alumina column with a mixture of toluene and ethyl acetate (15%), and in a silica gel column with a mixture of chloroform and methanol (2%). Despite of the repeated chromatography the resulting product is not pure, but it is a mixture of cyclosporins A and B.

According to a process disclosed in U.S. Pat. No. 4,215,199 a mixture of mainly cyclosporins A and B obtained from a fermentation liquor by repeated extraction with ethylene chloride subsequent to mechanical treatment in methanol, is first defatted with a 98:2 v/v mixture of chloroform and methanol on a silica gel column. The eluate is then evaporated to dryness. The residue is dissolved in methanol and is subjected to chromatography in a Sephadex LH20 column using methanol as eluent. The eluate is dissolved in a 98:2 v/v mixture of chloroform and methanol and is again subjected to chromatography in a silica gel column. Cyclosporin A appears first in the eluate, followed by cyclosporin B. The pure components are obtained by evaporating the eluates.

A method is disclosed in Helv. Chim. Acta 59, (4), p. 1075-92 for the separation of mixtures containing cyclosporins A and B. According to this method a fermentation liquor containing cyclosporins A and C is mixed with n-butyl acetate and is mechanically treated in a Westfalia separator. The organic phase is evaporated after that treatment, and the crude cyclosporin mixture is defatted with methanol and petroleum ether. After evaporation the residue is dissolved in chloroform and is subjected to chromatography by gradient elution with 98:5:1.5 v/v and 97:3 v/v mixtures of chloroform and methanol as eluent. Cyclosporin A, appears in the first eluent, cyclosporin B can be found in the second one. The pure crystalline produced is obtained by further chromatography. Fraction A is dissolved in methanol and is subjected to chromatography in a Sephadex LH-20 column by using methanol as eluent. The peak fractions are evaporated, dissolved in toluene and subjected to chromatography in a column packed with aluminium oxide, using toluene as eluent, in the presence of an increasing concentration of acetic ester. The fractions are then evaporated and are treated with activated carbon in an alcohol solution to obtain the crystalline product. The crude fraction C is dissolved in methanol and is eluted with methanol in a Sephadex-LH 20 packed column. The peak fractions are dissolved in diethylether and the cyclosporin C is separated by chromatography in a column packed with silica gel, using a 98:2 v/v mixture of chloroform and ethanol as eluent.

The foregoing chromatographic methods for the separation of cyclosporin mixtures are rather lengthy and expensive. The repeated liquid extraction and evaporation steps and the chromatographic operations that follow render these processes uneconomical and unsuitable for industrial scale application.

DESCRIPTION OF THE INVENTION

The aim of the present invention is to provide a purification method enabling both the separation of cyclosporin mixtures, and the purification of cyclosporin A, which method is economical and feasible on industrial scale and can be carried out more readily than the known processes.

Cyclosporin mixtures obtained from fermentation liquors comprise cyclosporin components having differing chromatographic characteristics, especially the cyclosporins A, B, and C, and also those impurities that are more apolar or more polar than cyclosporin A. The major part of these impurities consists of other cyclosporin components or contaminations that are similar to them.

Considering the fact that both the valuable components are the impurities that are very similar in chromatographic characteristics, favorable separation cannot be achieved in a single step, regardless of the employed solvent mixture. This is, because of the overlapping of the chromatographic peaks. Further chromatographic purification has to be carried out for obtaining certain components in pure form.

The present invention is based on the recognition that a favorable separation of the components can be achieved by subjecting mixtures containing different cyclosporin components to heat treatment prior to chromatography. Furthermore, cyclosporin A can be isolated in high purity in that manner. The purification and the one step chromatographic operation can be carried on readily and economically in accordance with the present invention.

DESCRIPTION OF THE DRAWINGS

The invention is described with reference being had to the drawing, wherein FIGS. 1 and 2 each show comparisons between the results of processes of the present invention and controls carried out in accordance with the prior an.

DETAILED DESCRIPTION OF THE INVENTION

The heat treatment of the present invention that precedes the chromatography, involves heating the mixture to a temperature sufficient for melting it. Melt formation occurs at a temperature between about 80° C.

and about 115° C. depending on the purity of the crude product. The melt is maintained at that temperature for a period of at least between about half an hour and about one hour, and then is allowed to cool slowly (in about 5 hours) to from about 20° C. to about 25° C. The heat treated product is then subjected to chromatography.

According to our experience not only solid mixtures can be subjected to heat treatment to achieve a better separation during the chromatography, but a similar result can also be achieved by heat treating the evaporation residue of a solid mixture obtained from a solution in the manner specified above.

Chromatography can be suitably carried out be sequentially charging the following sets of solvent mixtures chloroform:methylene chloride:ethanol (48:50:2), and then chloroform:ethyl acetate:ethanol (48:50:2); or acetone:methylene chloride (18:20), and then acetone:-methy The heat treatment preceding the chromatography results in a more favorable separation when any of the above exemplified solvent mixtures is employed. Cyclosporin A can be obtained in particularly high purity when the first set of solvent mixtures with three components were used.

Figure 1:
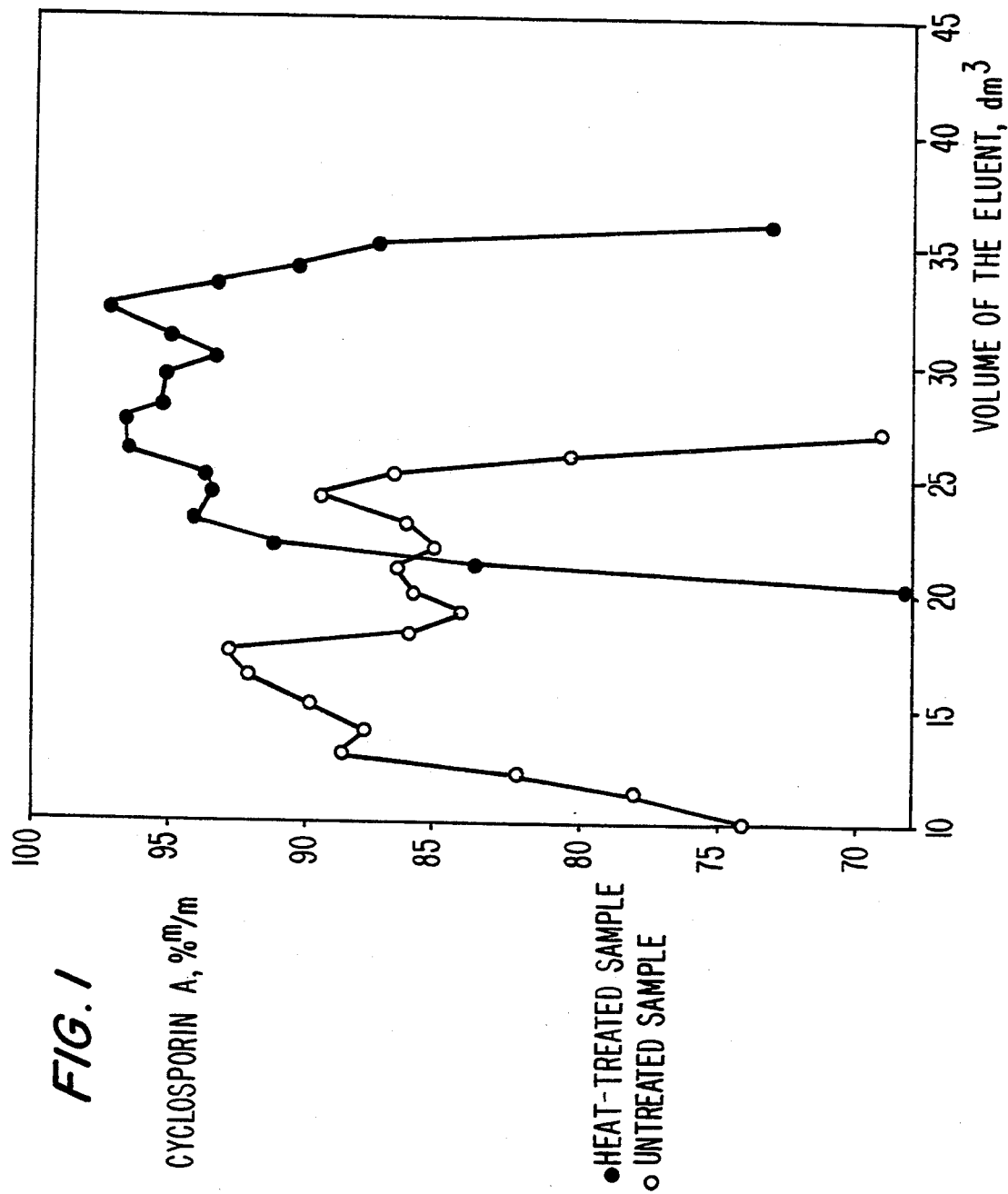
Figure 2:
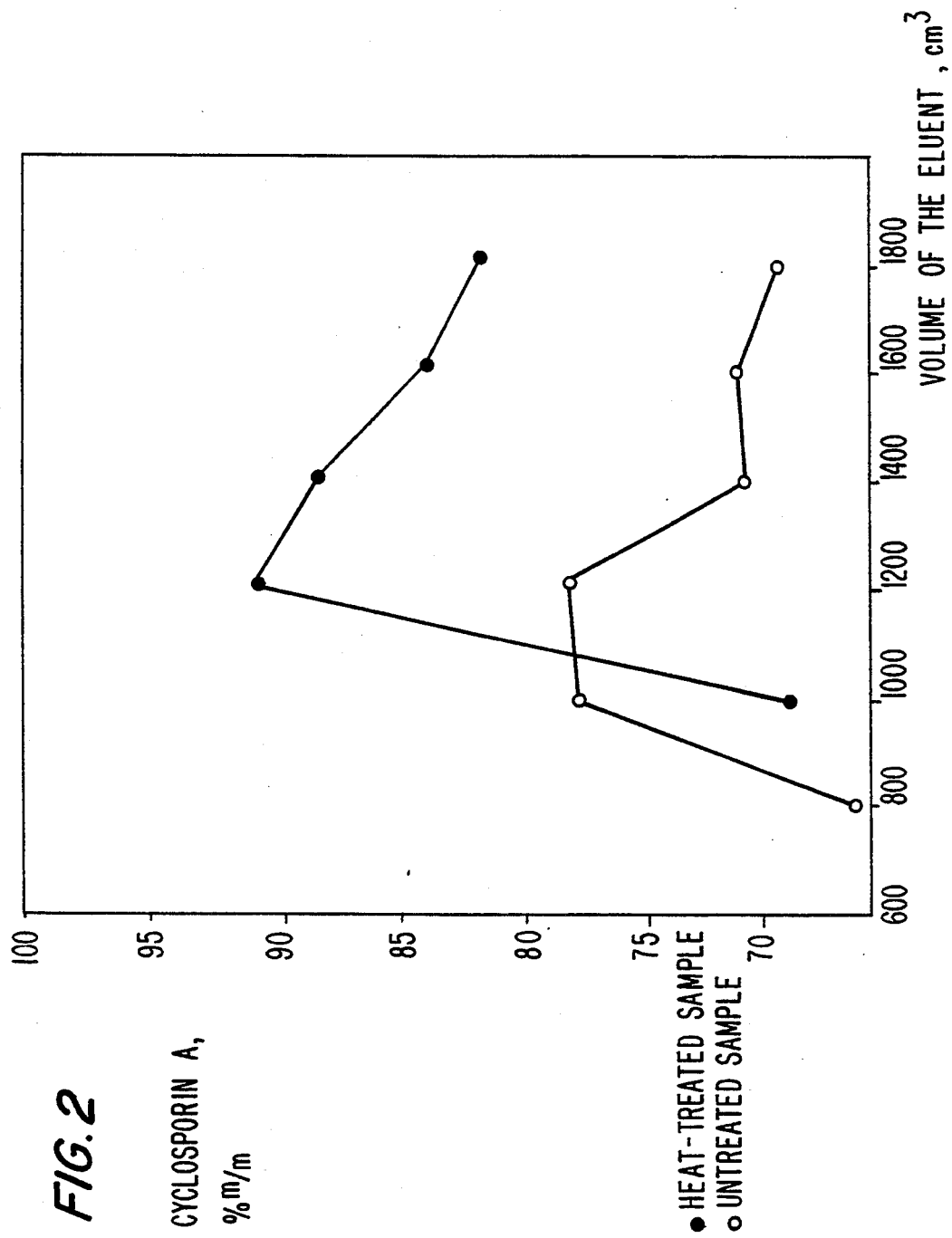

Comparative experiments were carried out for the chromatographic separation of heat treated and not heat treated cyclosporin mixtures of identical compositions using the exemplified solvent mixtures as eluents. The result are show in FIGS. 1 and 2. The purification of the product obtained from the specified fraction is plotted in % m/m against the volume of the eluent in dm$^3$. It can be seen that a surprisingly more favorable separation of the components can be achieved in the case of the heat treated samples in accordance with the present invention.

Control 1

A 280 g staring mixture of 51.36% m/m cyclosporin A, 7.92% m/m cyclosporin B, and 7.92% m/m cyclosporin C was employed. The chromatographic apparatus was an axially compressed preparative liquid chromatograph of 4 dm$^3$ volume, packed with silica gel having particle sizes ranging from 63 to 200 μm.

Axial hydraulic pressure of 10 bar was employed at a flow rate of 60 cm$^3$/min. Eluent 1 was a 48:50:2 mixture of CHCl$_3$:CH$_2$Cl$_2$:EtOH; and eluent 2 was a 48:50:2 of CHCl$_3$:EtOAc:EtOH. The mixture was dissolved in 1 dm$^3$ of eluent 1 and transferred to the column. Elution was started with eluent 1, and when 20 dm$^3$ had been consumed it was continued with eluent 2. The results shown in the following table were obtained. The solvent mixture change to eluent 2 is indicated with a double asterisk. "CA" means the amount of cyclosporin A calculated on the dry substance. The yield of cyclosporin A was 20.26 g, or 14.08% m/m, at a purity of greater than 90% m/m.

| Eluent dm$^3$ | Evaporated substance g | CA % m/m | CB % m/m | Drying loss % m/m | $^m$CA g | CA* % m/m |
|---|---|---|---|---|---|---|
| 9 | 10.0 | — | — | — | — | — |
| 10 | 19.48 | 72.26 | — | 2.39 | 14.61 | 74.04 |
| 11 | 21.47 | 74.95 | — | 4.72 | 17.32 | 78.67 |
| 2 | 12.94 | 80.59 | — | 2.34 | 10.73 | 82.56 |
| 13 | 10.26 | 88.29 | — | 1.75 | 9.23 | 89.42 |
| 14 | 9.30 | 86.64 | — | 1.65 | 8.21 | 88.15 |
| 15 | 8.95 | 89.13 | — | 1.45 | 8.10 | 90.44 |

-continued

| Eluent dm$^3$ | Evaporated substance g | CA % m/m | CB % m/m | Drying loss % m/m | $^m$CA g | CA* % m/m |
|---|---|---|---|---|---|---|
| 16 | 7.25 | 90.99 | — | 1.65 | 6.71 | 92.52 |
| 17 | 5.85 | 92.11 | — | 1.18 | 5.45 | 93.22 |
| 18 | 4.99 | 84.74 | — | 1.57 | 4.30 | 86.12 |
| 19 | 4.06 | 82.55 | — | 2.46 | 3.45 | 84.65 |
| 20 | 3.55 | 84.31 | — | 1.87 | 3.05 | 86.00 |
| 21** | 2.52 | 64.37 | — | 2.22 | 2.18 | 86.42 |
| 22 | 2.48 | 82.59 | — | 3.25 | 2.12 | 85.37 |
| 23 | 1.98 | 82.86 | — | 3.93 | 1.71 | 86.22 |
| 24 | 18.67 | 88.34 | — | 1.48 | 16.77 | 89.68 |
| 25 | 9.44 | 85.52 | — | 1.48 | 8.21 | 86.80 |
| 26 | 7.03 | 79.10 | — | 1.32 | 5.65 | 80.24 |
| 27 | 6.57 | 67.96 | 15.88 | 1.53 | 4.75 | 69.11 |
| 28 | 7.21 | 35.66 | 45.73 | 1.47 | 2.67 | 36.21 |
| 29 | 4.95 | 10.84 | 62.37 | 1.25 | 0.59 | 10.99 |
| 30 | 2.30 | 3.52 | 64.57 | 0.61 | 0.09 | 3.55 |
| 31 | 0.40 | 3.09 | 68.82 | 0.49 | 0.01 | 3.16 |
| 32 | 1.00 | 3.22 | 69.05 | 0.52 | 0.03 | 3.23 |
| 33 | 0.85 | — | 75.99 | 0.33 | — | — |
| 34 | 1.83 | — | 76.05 | 0.46 | — | — |
| 35 | 2.20 | — | — | — | — | — |

EXAMPLE 1

The process of Control 1 was repeated under identical circumstances except that before chromatography the mixture was subjected to heat treatment at a temperature of about 110° C. for one hour under ambient atmosphere, and cooled to about 20° C. within 5 hours while exposed to ambient conditions. The melt was dissolved in 1 dm$^3$ of eluent 1 and transferred to the column. Eluent 2 was employed after 27 dm$^3$ of eluent 1 was employed. The results are summarized in the following table. A total yield of 118.8 g or 77.75% m/m was obtained with a purity of over 90% m/m. In fact, 21.03 g of the yield (14.62%) had a purity higher than 97.5 % m/m.

| Eluent dm$^3$ | Evaporated substance g | CA % m/m | CB % m/m | Drying loss % m/m | $^m$CA g | CA* % m/m |
|---|---|---|---|---|---|---|
| 31 | 15.59 | 93.54 | — | 1.68 | 14.84 | 95.18 |
| 32 | 21.55 | 94.76 | — | 2.87 | 21.03 | 97.56 |
| 33 | 8.93 | 91.68 | — | 2.01 | 8.36 | 93.56 |
| 34 | 4.33 | 89.13 | 0.38 | 1.42 | 3.92 | 90.59 |
| 35 | 2.79 | 86.12 | 0.84 | 1.42 | 2.44 | 87.37 |
| 36 | 6.72 | 72.30 | 14.98 | 1.05 | 4.92 | 73.17 |
| 37 | 6.92 | 13.39 | 46.49 | 1.76 | 1.04 | 13.64 |
| 38 | 2.82 | 9.05 | 72.50 | 1.41 | 0.29 | 9.18 |
| 39 | 1.02 | 7.43 | 69.24 | 0.89 | 0.08 | 7.50 |
| 40 | 1.07 | 5.0 | 67.09 | 1.42 | 0.06 | 5.60 |
| 41 | 1.10 | 6.79 | 69.63 | 3.52 | 0.11 | 7.04 |
| 42 | 0.89 | 4.06 | 68.15 | 4.29 | 0.07 | 4.25 |
| 43 | 1.20 | 4.24 | 77.21 | 4.78 | 0.10 | 4.46 |
| 44 | 1.13 | 2.83 | 90.51 | 0.10 | 0.03 | 2.83 |
| 45 | 1.34 | 1.72 | 85.29 | — | 0.02 | — |
| 46 | 1.44 | 1.63 | 80.80 | 0.92 | 0.03 | — |

Control 2

A 50 g starting mixture of 61.48% m/m cyclosporin A, 9.41% m/m cyclosporin B, and 7.47% m/m cyclosporin C was dissolved in 350 ml methylenechloride. The liquid chromatograph had a 700 cm$^3$ volume packed with Merck silica gel having particle sizes ranging from 63 to 200 μm.

The flow rate was 3 cm$^3$/min. Eluent 1 was a ratio of 18:82 of an acetone:methylene chloride solvent mixture, and eluent 2 was an acetone:methylene chloride solvent mixture at a volume ratio of 20:80.

The results are shown in the following table. None of the resulting product had a purity exceeding 90% m/m. The cyclosporin A content of the fraction having the highest active ingredient content was 78.7%, corresponding to 8.4 g of pure cyclosporin A.

| Eluent dm$^3$ | Evaporated substance g | % m/m | CB % m/m | Drying loss % m/m | $^m$CA g | CA* % m/m |
|---|---|---|---|---|---|---|
| 200 | — | — | — | — | — | — |
| 400 | — | — | — | — | — | — |
| 600 | — | — | — | — | — | — |
| 800 | 8.38 | 66.38 | — | 0.44 | 5.56 | 66.67 |
| 1000 | 10.82 | 77.66 | — | 1.0 | 8.40 | 78.76 |
| 1200 | 4.26 | 77.71 | — | 0.99 | 3.31 | 78.48 |
| 1400 | 2.88 | 71.23 | 0.22 | 1.26 | 2.05 | 72.13 |
| 1600 | 1.99 | 71.64 | 0.50 | 1.83 | 1.42 | 72.97 |
| 1800 | 1.45 | 68.16 | 1.03 | 1.35 | 0.98 | 69.09 |
| 2000 | 1.12 | 72.41 | 1.42 | 0.35 | 0.81 | 72.66 |
| 2200 | 1.09 | 59.57 | 1.60 | 1.12 | 0.64 | 60.24 |
| 2400 | 0.89 | 63.17 | 2.22 | 0.64 | 0.56 | 59.73 |
| 2600 | 0.78 | 59.35 | 2.64 | 0.64 | 0.46 | 59.73 |
| 2800 | 0.85 | — | — | — | — | — |
| 3000 | 0.53 | 50.02 | 4.06 | 0.70 | 0.26 | 50.35 |
| 3200 | 0.74 | — | — | — | — | — |
| 3400 | 0.40 | 40.65 | 4.32 | 0.73 | 0.16 | 40.94 |
| 3600 | 0.40 | 30.78 | 4.17 | 0.51 | 0.12 | 30.15 |
| 3800 | 0.63 | — | — | — | — | — |
| 4000 | 0.48 | — | — | — | — | — |
| 4200 | 0.40 | — | — | — | — | — |
| 4400 | 0.40 | — | — | — | — | — |
| 4600 | 0.20 | — | — | — | — | — |
| 4800** | 0.26 | — | — | — | — | — |
| 5000 | 0.50 | — | — | — | — | — |
| 5200 | 0.25 | — | — | — | — | — |
| 5400 | 0.07 | — | — | — | — | — |
| 5600 | 0.03 | — | — | — | — | — |
| 5800 | 0.06 | — | — | — | — | — |
| 6000 | 0.06 | — | — | — | — | — |
| 6200 | 0.04 | — | — | — | — | — |
| 6400 | 11.48 | 2.38 | 0 | 0.57 | 0.27 | 0.39 |
| 6600 | 0.25 | — | — | — | — | — |

EXAMPLE 2

The conditions were the same as in Control 2, except that the 50 g of the starting mixture was first heat treated for 1 hour at about 110° C. The melt was cooled, dissolved in 350 cm$^3$ methylene chloride and transferred to the column.

The results are tabulated below. A yield of 11.94 g, corresponding to 38.89% of a purity of over 90% m/m was obtained.

| Eluent dm$^3$ | Evaporated substance g | CA % m/m | CB % m/m | Drying loss % m/m | $^m$CA g | CA* % m/m |
|---|---|---|---|---|---|---|
| 600 | — | — | — | — | — | — |
| 800 | 0.29 | — | — | — | — | — |
| 1000 | 5.4 | 68.50 | — | 0.33 | 3.69 | 68.72 |
| 1200 | 13.26 | 90.09 | — | 1.37 | 11.94 | 91.34 |
| 1400 | 4.48 | 88.20 | - | 0.50 | 3.95 | 88.64 |
| 1600 | 2.84 | 84.41 | 0.39 | 0.34 | 2.39 | 84.69 |
| 1800 | 1.98 | 81.88 | 0.87 | 0.46 | 1.62 | 82.25 |
| 2000 | 1.38 | 78.16 | 1.30 | 0.44 | 1.07 | 78.50 |
| 2200 | 1.49 | 77.40 | 1.92 | 1.37 | 1.15 | 78.47 |
| 2400 | 0.95 | 70.80 | 2.26 | 1.14 | 0.67 | 71.61 |
| 2600 | 0.75 | 66.99 | 3.09 | 0.34 | 0.50 | 67.21 |
| 2800 | 0.60 | 64.78 | 4.07 | 0.66 | 0.38 | 65.21 |
| 3000 | 0.39 | 58.07 | 5.34 | 0.63 | 0.22 | 58.43 |
| 3200 | 0.45 | 53.11 | 5.22 | 0.31 | 0.23 | 53.27 |
| 3400 | 0.41 | 46.48 | 5.84 | 0.47 | 0.19 | 46.69 |
| 3600 | 0.37 | — | — | — | — | — |
| 3800 | 0.34 | — | — | — | — | — |
| 4000 | 0.23 | — | — | — | — | — |
| 4200 | 0.27 | — | — | — | — | — |
| 4400 | 0.19 | — | — | — | — | — |
| 4600 | 0.16 | — | — | — | — | — |
| 4800 | 0.10 | — | — | — | — | — |
| 5000** | 0.20 | — | — | — | — | — |
| 5200 | 0.15 | — | — | — | — | — |
| 5400 | 0.18 | — | — | — | — | — |
| 5600 | 0.28 | — | — | — | — | — |
| 5800 | 0.10 | — | — | — | — | — |
| 6000 | 0.04 | — | — | — | — | — |
| 6200 | 5.23 | 2.52 | 43.28 | 0.48 | 0.13 | 2.49 |
| 6400 | 4.59 | — | 6.82 | 0.56 | — | — |
| 6600 | 0.62 | — | 0.87 | 0.34 | — | — |
| 6800 | 0.06 | — | — | — | — | — |

The results of comparative experiments involving the purification of untreated cyclosporin mixtures and mixtures heat treated in accordance with the present invention, involving the mass of the product obtained in a purity exceeding 90% m/m, and the yield in %, are shown in the following table.

| | Untreated mixture | | Heat treated mixture | |
|---|---|---|---|---|
| | Control 1 | Control 2 | Example 1 | Example 2 |
| Mass of cyclosporin A: | 20.26 g | 0.0 g | 111.80 | 11.94 g |
| Yield: | 14.08% | 0.0% | 77.75% | 38.89% |
| Cyclosporin A (>97.5% m/m): | 0.0 g | 0.0 g | 21.03 g | 0.0 g |
| Yield: | 0.0% | 0.0% | 14.62% | 0.0% |

From the above table it can be seen that in the case of the products heat treated in accordance with the present invention a considerably higher amount of substance can be isolated in a purity exceeding 90% m/m due to the better separation. It can also be established that when starting from heat treated products and using solvent mixtures chloroform:methylene chloride:ethanol (48:50:2), and chloroform:methylene chloride:ethanol (48:50:2) it becomes possible to obtain cyclosporin A in a single step in a purity of 97.5 m/m required by the U.S. Pharmacopoeia. The yield of the product obtained in a quality required by the U.S. Pharmacopoeia is practically identical to the yield of all the products obtained in purity exceeding 90% m/m when subjecting an untreated product to chromatography.

EXAMPLE 3

A 50 g staring mixture of 30.74% m/m cyclosporin A, 4.7% m/m cyclosporin B, and 3.7% m/m cyclosporin C was dissolved in methylene chloride and then evaporated. The residue was subjected to heat treatment at a temperature of about 80° C. for about 2 hours and then processed exactly as in Example 2.

The results are summarized in the following table. No fraction having an active ingredient content exceeding 90% could be isolated. The cyclosporin A content of the fraction having the highest active ingredient content was 87.08% corresponding to 3.36 g of pure cyclosporin A.

| Eluent dm$^3$ | Evaporated substance g | CA % m/m | CB % m/m | Drying loss % m/m | $^m$CA g | CA* % m/m |
|---|---|---|---|---|---|---|
| 800 | — | — | — | — | — | — |
| 1000 | 8.95 | 74.32 | — | 0.05 | 6.65 | 74.93 |

-continued

| Eluent dm³ | Evaporated substance g | CA % m/m | CB % m/m | Drying loss % m/m | $^m$CA g | CA* % m/m |
|---|---|---|---|---|---|---|
| 1200 | 8.56 | 85.33 | — | 1.45 | 7.30 | 86.53 |
| 1400 | 3.91 | 86.03 | — | 1.38 | 3.36 | 87.68 |
| 1600 | 2.72 | 84.20 | 0.42 | 0.58 | 2.29 | 84.68 |
| 1800 | 1.94 | 76.74 | 0.47 | 0.96 | 1.48 | 77.02 |
| 2000 | 1.54 | 84.71 | 1.13 | 0.38 | 1.30 | 84.73 |
| 2200 | 1.28 | 84.95 | 1.78 | 0.42 | 1.08 | 85.28 |
| 2400 | 1.04 | 85.38 | 2.36 | 0.36 | 0.88 | 85.68 |
| 2600 | 1.02 | 84.25 | 3.51 | 0.28 | 0.85 | 84.45 |
| 2800 | 0.76 | 82.36 | 4.27 | 0.38 | 0.62 | 82.55 |
| 3000 | 0.56 | 78.25 | 4.85 | 0.54 | 0.43 | 78.63 |
| 3200 | 0.48 | 76.38 | 4.25 | 0.64 | 0.36 | 76.74 |
| 3400 | 0.47 | — | — | — | — | — |
| 3600 | 0.42 | — | — | — | — | — |
| 3800 | 0.62 | — | — | — | — | — |
| 4000 | 0.32 | — | — | — | — | — |
| 4200 | 0.54 | — | — | — | — | — |
| 4400 | 0.56 | — | — | — | — | — |
| 4600 | 0.54 | — | — | — | — | — |
| 4800 | 0.54 | — | — | — | — | — |
| 5000** | 0.61 | — | — | — | — | — |
| 5200 | 0.78 | — | — | — | — | — |
| 5400 | 0.92 | — | — | — | — | — |
| 5600 | 0.62 | — | — | — | — | — |

We claim:

1. A process for the solution chromatographic purification of cyclosporin A from a starting mixture containing cyclosporin A and one or more of cyclosporin B, C, other cyclosporin components that are more polar or more apolar than cyclosporin A, and other like contaminants, which comprises heating the starting mixture or an evaporation residue thereof to form a melt, cooling the melt, and carrying out solution chromatography of the cooled material.

2. The process of claim 1, wherein the solution chromatography is carried out first in a mixture of the solvents chloroform, dichloromethane, and ethanol, and then in a mixture of the solvents chloroform, ethylacetate, and ethanol.

3. The process of claim 2, wherein each of said solvent mixtures comprises the solvents in a ratio of about 48:50:2.

4. The process of claim 1, wherein said heating comprises melting the material at a temperature of from about 80° C. to about 115° C.

5. The process of claim 1, wherein said melt is rested at said melting temperature.

6. The process of claim 5, wherein said resting is carried out for a period of from about ½ an hour to 1 hour.

7. The process of claim 1, wherein said cooling comprises cooling the melt to from about 20° C. to about 25° C.

8. The process of claim 5, wherein said cooling comprises cooling the melt within a period of about 5 hours.

9. The process of claim 4, wherein, said cooling comprises cooling the melt to from about 20° C. to about 25° C.

10. The process of claim 1, wherein said cooling comprises cooling the melt within a period of about 5 hours.

* * * * *